US00RE34818E

United States Patent [19]

Daneman et al.

[11] E Patent Number: Re. 34,818

[45] Reissued Date of Patent: Jan. 3, 1995

[54] KNEE BRACE WITH ARTICULATING BRACE HINGE AXIS

[75] Inventors: Alexis G. Daneman, Danville, Calif.; Jean-Paul Nielsen, Corvallis, Oreg.

[73] Assignee: Orthopedic Technology, Inc., Tracy, Calif.

[21] Appl. No.: 36,750

[22] Filed: Mar. 25, 1993

Related U.S. Patent Documents

Reissue of:

[64] Patent No.: 5,078,127
Issued: Jan. 7, 1992
Appl. No.: 652,144
Filed: Feb. 6, 1991

[51] Int. Cl.[6] ..... A61F 5/00
[52] U.S. Cl. ..... 620/26; 602/16
[58] Field of Search ..... 602/16, 23, 26

[56] References Cited

U.S. PATENT DOCUMENTS

| | | | |
|---|---|---|---|
| 4,372,298 | 2/1983 | Lerman | 602/26 |
| 4,503,846 | 3/1985 | Martin | 128/88 |
| 4,624,247 | 11/1986 | Ford | 602/26 |
| 4,732,143 | 3/1988 | Kausek et al. | 128/80 F |
| 4,790,299 | 12/1988 | Marquette | 128/80 F |
| 4,791,916 | 12/1988 | Paez | 602/26 |
| 4,802,466 | 2/1989 | Meyers et al. | 128/88 |
| 4,803,975 | 2/1989 | Meyers | 602/26 |
| 4,854,308 | 8/1989 | Drillio | 128/80 F |
| 4,940,045 | 7/1990 | Cromartie | 128/80 F |

*Primary Examiner*—Richard J. Apley
*Assistant Examiner*—Lynne A. Reichard
*Attorney, Agent, or Firm*—Townsend and Townsend Khourie and Crew

[57] ABSTRACT

An activity knee brace is disclosed in which the hinge axis of the brace articulates to overlie during knee flexure the moving center of pivot of the condylar of the femur with respect to the plateau of the fibula tibia. The brace consists of a thigh portion, a lower leg portion, and a hinge axis therebetween. The thigh portion supports the brace in the thigh. The lower leg portion supports the brace to the lower leg. The hinge axis is designed to overlie the point of pivot of the knee. Articulating of the activity brace hinge axis occurs from the thigh portion. The thigh portion is braced at the upper end of the thigh. The thigh portion is braced at the lower end at the medial supracondylar area by pad and adjustable strap system contacting and locating on the supracondylar hollow on the inside of the upper leg. The pads at the lower thigh portion of the brace are mounted at a pivotal axis. This pivotal axis is offset with respect to the hinge axis at a distance approximately 1⅛th inches. During movement of the brace knee between extension and flexion, the pivotal movement of the supracondylar pads causes the hinge axis of the brace to articulate. The disclosed articulation imparted to the hinge axis of the brace tracks in large the moving point of pivot of the knee. Consequently, an activity brace is disclosed having improved reinforcement of the knee at a simple hinge axis.

5 Claims, 3 Drawing Sheets

KNEE BRACE WITH ARTICULATING BRACE HINGE AXIS

Matter enclosed in heavy brackets [ ] appears in the original patent but forms no part of this reissue specification; matter printed in italics indicates the additions made by reissue.

*This application is a reissue of application Ser. No. 07/652,144 filed Feb. 6, 1991, now U.S. Pat. No. 5,078,127 issued Jan. 7, 1992.*

This invention relates to knee braces. More particularly, the disclosed knee brace is an activity type brace useful for reinforcing the knee during activity or alternatively useful with a lower leg prothesis to support the prothesis and keep it properly positioned during use.

BACKGROUND OF THE INVENTION

Knee braces are known. They typically include a thigh member for fastening to the thigh, a lower leg member for fastening to the lower leg and a hinge axis therebetween positioned over the knee to be reinforced. All manner of straps for securing the respective leg and thigh portions have been illustrated in the prior art.

1. Brief Description of the Relevant Art

The following prior art includes a representative sample of such prior art.

Some knee braces have included compound hinges. Such compound hinges include two or more pivot points closely spaced along the natural joint defined by the knee. Examples of such compound hinges include Lerman U.S. Pat. No. 4,372,298; Marquette U.S. Pat. No. 4,793,333; Kausek et al. 4,732,143; and European Patent Application 0173161 to Townsend.

A knee stabilizer is disclosed in Marquette U.S. Pat. No. 4,790,299 having a supracondylar support. This supracondylar support provides vertical location of the brace on the leg at the supracondylar hollow.

Many braces rely on a simple hinge axis rigidly braced with respect to the knee. Example of such devices include Ford U.S. Pat. No. 4,624,247; Martin et al. U.S. Pat. No. 4,503,846 and Myers et al. U.S. Pat. No. 4,802,466.

There is a known tendency of some knee braces to "piston" with respect to the leg. Such piston movement can be accommodated by various springs between the respective knee brace portions. Illustrative of such a spring arrangement is Carsalade British Patent Application 2,156,221.

2. State of the Problem

The knee, unlike the common hinge, has an asymmetrical hinging action. As the knee bends, the pivot point about which the bending occurs, changes. Reference to the views provided by 5, 6 and 7 of this application can illustrate this point.

It is to be noted at this juncture in the description, that insofar as recognition of the problem to be solved constitutes invention, invention is claimed in fully understanding knee movement and relating it to the mechancis of the disclosed activity brace.

In FIGS. 5–7 a typical knee joint is illustrated in rotation. The outlines of a femur E, a tibia T and a fibula F are illustrated within a normal leg having conventionally proportioned tissue. The knee is shown in rotation from an extended disposition as shown in FIG. 5 to a position approximately maximum flexion as shown in FIG. 7. Intermediate rotational positions are shown in FIG. 6.

Some reference to the skeletal anatomy of the knee is beneficial. The lower leg includes a fibula F and the tibia T. These bones have their upper surface jointly defining a plateau K upon which the corresponding condylar of the femur turns. Applicable cartilage, ligaments, and muscle are, of course, omitted.

For reference in the following discussion, the tibia has been provided with a center line 100. The reader will understand that as this discussion proceeds that the center of rotation of the condylar of the femur changes with respect to the center line during movement of the knee between the extended and flexed positons.

The femur E includes a condylar C. Condylar C is not symmetrical with respect to the femur. This can be seen by inspecting FIG. 5. As in the case of the tibia, the femur E has been given a center line 102. This center line will also be used to discuss the asymmetry of the knee joint requiring the improvement of this invention.

Femur E normally rests upon the plateau K of the tibia at surface 9. However, upon flexion, resting occurs on the surface 10 at condylar K. It is apparent at first glance that the illustrated "hinge action" of the knee is not symmetrical. This phenomena can be further understood by referring to the respective "centers of rotation" of the condylar of the femur overlying the lower leg.

When the knee first begins to rotate from a position of extension to a position of flexion, turning of the joint of the knee first occurs about a center 110. It can be seen that this center 110 is to the left of the center line 100 of the fibula tibia and also to the left of the center line 102 of the femur E.

When the knee finishes rotation to a point of maximum flexion illustrated in FIG. 10, final turning occurs about a center 120. It can be seen that this center in FIG. 7 has moved to the right of center line 100 of the fibula tibia.

Referring to FIG. 6, an attempt to trace the migration of the center of pivot with respect to the condylar K and the tibia is instructive. Specifically, the center of pivot moves along a line 130 as the leg moves from extension deflection. This begins with the extension center of pivot 110 on the left and ends with the flexion center of pivot 120 on the right.

Once this diagram is seen and understood, the futility of providing a knee with a simple hinge for reinforcement of the knee can be clearly understood.

Assume that the full dynamic load is placed on the knee joint and the brace together during active body movement. As set forth in the prior art, assume that the brace holds a hinge axis as rigidly as possible at one rigid hinge axis location with respect to the knee joint. However, the knee, undergoing both flexion and extension will have its center of pivot moved with respect to the rigid hinge axis. As all those familiar with the simple concept of mechancis know, something relative to the knee with its moving center of pivot, the brace (or both) has to give in order to permit hinging axis. Indeed, a recitation of undesirable knee brace motions can catalog such conforming movements of the knee relative to a brace to permit the required hinge like movement of the knee joint.

Where the hinge axis of the brace is rigidly held with respect to the knee joint, a phenomena commonly known a "pistoning" frequently occurs. Either the thigh portion or the lower leg portion (or both) move up and down with respect to the thigh or lower leg. Absent such movement, bending of the knee could not occur. Skin abrasions and flesh irritations are a common result of such "pistoning" movement.

This dynamic misalignment between the rigid hinge axis of a knee brace and the moving center of pivot of a knee also causes discomfort to the reinforced knee joint itself. As those familiar with mechancis know, two closely positioned but misaligned hinge axes acting on the same levers (the thigh and the lower leg) work against each other with considerable force. This considerable force can cause discomfort at the knee joint and even damage to the reinforced knee over a period of time.

Clearly there is a need to emulate in a knee brace, especially an activity knee brace, movement to the braced hinge axis which correspond in large measure to the movement of the knee center of rotation.

Compound hinges utilized with some knee braces having more than two centers of pivot within a hinge element. These compound hinges have in large measure been unsatisfactory to accommodate the dynamically changing center of pivot at the knee. Such compound hinge members must rely on the knee joint to cause bending reinforcement of the hinge joint. Frequently, such compound hinge elements can only follow the flexure of the knee taking their own support in proper flexure from the knee. Consequently, they cannot reinforce the flexure of the knee to the extent required.

SUMMARY OF THE INVENTION

An activity knee brace is disclosed in which the hinge axis of the brace articulates to overlie during knee flexure the moving center of pivot of the condylar of the femur with respect to the plateau of the fibula tibia. The brace consists of a thigh portion, a lower leg portion, and a hinge axis therebetween. The thigh portion supports the brace to the thigh. The lower leg portion supports the brace to the lower leg. The hinge axis is designed to overlie the point of pivot of the knee. Articulating of the activity brace hinge axis occurs from the thigh portion. The thigh portion is braced at the upper end of the thigh. The thigh portion is braced at the lower end of the medial supracondylar area by pad and adjustable strap system contacting and locating on the supracondylar hollow on the inside of the upper leg. The pads at the lower thigh portion of the brace are mounted at a pivotal axis. This pivotal axis is offset with respect to the hinge axis at a distance approximately 1⅛th inches. During movement of the brace knee between extension and flexion, the pivotal movement of the supracondylar pads causes the hinge axis of the brace to articulate. The disclosed articulation imparted to the hinge axis of the brace tracks in large the moving point of pivot of the knee. Consequently, an activity brace is disclosed having improved reinforcement of the knee at a simple hinge axis.

Other Objects, Features and Advantages

An advantage of the disclosed activity brace is that movement of the thigh portion and the lower leg portion of the brace with respect to the thigh and lower leg is reduced. The tendency for the leg movement known as pistoning within the disclosed brace is decidedly reduced.

A further advantage of this invention is that the misalignment and dynamic forces which accompany the misalignment are also reduced. Consequently, the disclosed activity brace provides an improved level of comfort and an improved ability to provide the necessary support of the knee leading to recovery.

A further advantage of the disclosed design is that the dimension of offset between the hinge axis of the brace and the pivot of the supracondylar pads is generic to a large portion of the population. It has been found that for adults that the amount of offset between the hinge axis and the supracondylar pad pivot axis remains essentially unchanged. This is so even though the length and size of the person wearing the brace varies considerably. Accordingly, the dimension illustrated in the preferred embodiment of the disclosed brace finds a relatively universal application to the population at large.

Other objects, features and advantages of the invention will appear from the following description in which the preferred embodiment is set forth in detail in conjunction with the accompanying drawings.

BRIEF DESCRIPTION OF THE DRAWINGS

FIG. 1 illustrates a knee brace 2 made according to this invention. Knee brace 2 includes an upper brace portion 4 and a lower brace portion 6. Upper brace portion 4 includes a curved upper part 8 and a pair of upper struts 10. Similarly, lower brace portion 6 includes a curved lower part 12 in a pair of lower struts 14, only the medial upper and lower struts 10, 14 being illustrated in FIG. 1. Corresponding upper and lower struts 10, 14 are pivotally mounted to one another by knee brace pivot assembles 16. Each pivot assembly 16 is covered with a protective cover 18 in the embodiment of FIG. 1, such protective cover being removed in FIG. 4 for clarity.

Figure 1:
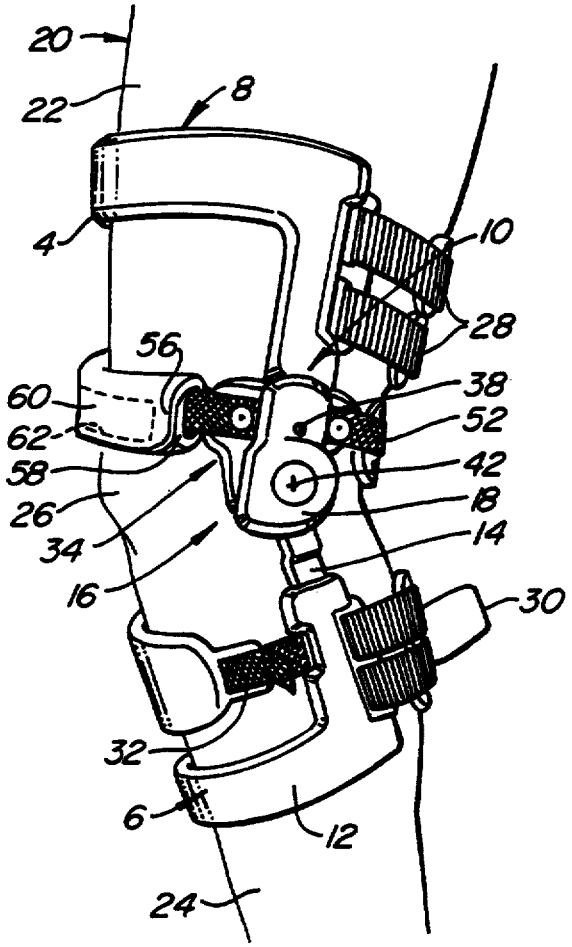
FIG. 1 is a perspective view of a knee brace made according to the invention shown mounted to a user's leg.

Knee brace 2 is mounted to the user's leg 20 with upper brace portion 4 secured to the user's upper leg 22 and with lower brace portion 6 secured to the user's lower leg 24, that is above and below the knee 26. Upper and lower straps 28, 20 are connected to upper and lower struts 10,14 and fit against the back of leg 20.

Figure 3:
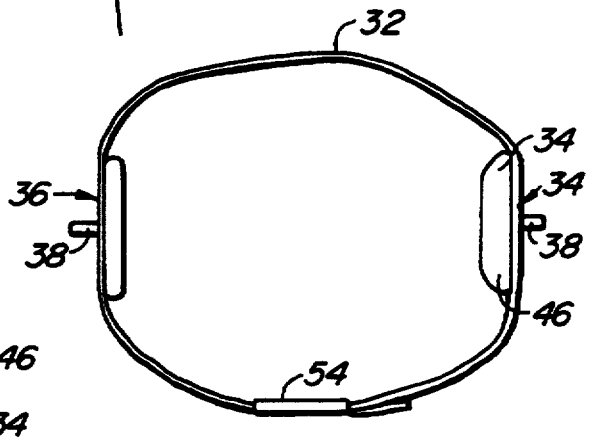
FIG. 3 is a simplified top view of the condylar pads and condylar strap of FIG. 2 without showing the user's leg.
Figure 2:
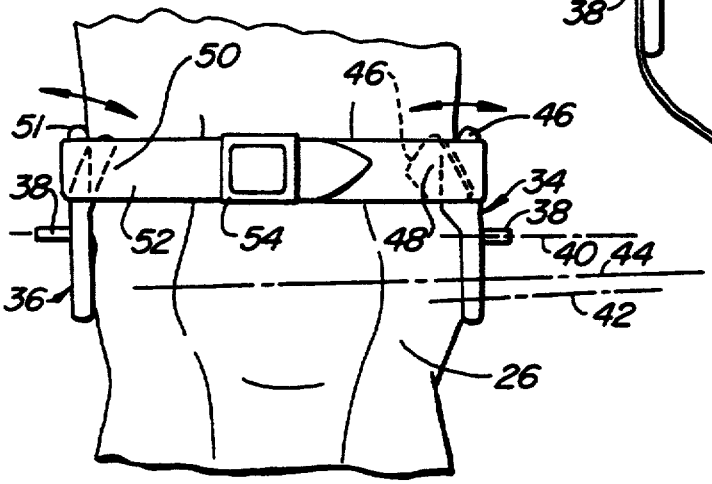
FIG. 2 is a simplified front view of a user's knee showing only the condylar pads and the adjustable condylar strap in place, with the inward deflection of the upper portions of the condylar pads, caused by increasing the tension on the condylar strap, is indicated by dashed lines.
Figure 4:
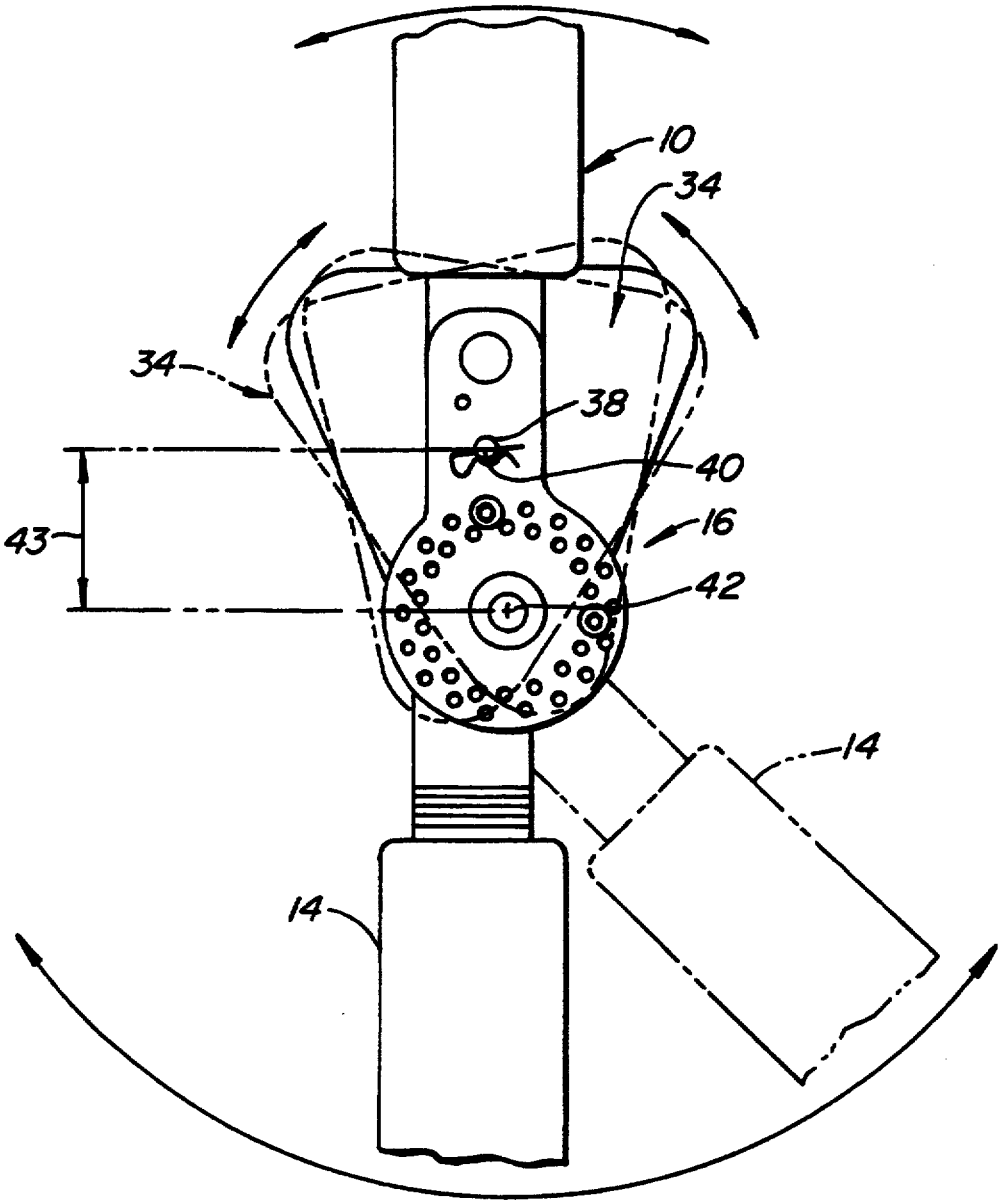
FIG 4 is an enlarged view of the medical knee brace pivot assembly of FIG. 1 with the padding removed for clarity, and showing different relative pivotal positions of the upper and lower struts of the medial condylar pads.

Knee brace 2 further includes a medial condylar pad 34, shown also in FIGS. 2–4, and a lateral condylar pad 36, shown also in FIGS. 2 and 3. Medial condylar pad 34 is pivotally mounted to upper strut 10 by pivot pin 38 so to pivot about a horizontal pivot axis 40. Pivot axis 40 is generally parallel to, but spaced- apart from, the knee brace pivot axis 42 of knee brace pivot assembly 16 by a distance 43.

I prefer to offset the pivot point of the condylar pads 34, 36 with respect to the hinge axis by an amount approximately 1⅛". It has been found that in the population at large, although the length of legs vary dramatically, the joint structure remains on a relative basis approximately of uniform dimension. Therefore the offset that I provide has relatively universal application in the adult population at large.

The above dimension can be varied and still carry out the intent of this invention. For example, from large to small humans it is conceivable that the offset of the pivot point of the condylar pads 34, 36 with respect to the knee joint could be in the range of ⅞" to 1⅜". As an intermediate range, this offset could be 1" to 1¼". The offset of 1⅛" is preferred.

It will be realized by those skilled in the art that extreme cases may require repositioning. For example, with respect to infants, reduction in dimension may well be required.

Returning to FIG. 1, it will be seen that knee 26 is free for some movement with respect to struts 10. It is this freedom of movement urged by the pivoting pads 34, 36 that enables the hinge axis 42 to overly the dynamically changing center of pivot of the knee joint.

FIG. 4 also shows different relative positions between upper and lower struts 10, 14 and different rotary positions of medial condylar pad 34, both illustrated by broken lines. Preferably the pivot axis 44 of knee 26 is positioned between pivot pad axis 40 and knee brace pivot axis 42 as illustrated in FIG. 2.

As suggested in FIGS. 2 and 3, lateral condylar pad 36 is generally flat while the upper portion 46 of medial condylar pad 34 is somewhat bulbous. These configurations are intended to better conform to the user's medial supracondylar hollow 48 and lateral supracondylar depression 50. To adjust the deflection of upper portion 46 of medial condylar pad 34 and the upper portion 51 of lateral condylar pad 36, that is to vary the inward deflection as suggested in FIG. 2, a condylar strap 52 is passed around upper portions 46, 51 of medial and lateral condylar pads 34, 36 and about the user's leg. The tension on strap 52 is adjusted through use of a buckle 54. Once adjusted, the outer ends 56, 58 of the padded cover 60 (see FIG. 1) can be placed over one another and secured in place through the use of hook and loop fasteners 62.

In use, the user loosens straps 28, 30, 32 and 52 to permit knee brace 2 to be properly positioned on leg 20 with medial and lateral condylar pads 34, 36 opposite the medial and lateral condyles of the user's leg. Straps 28, 30, 32 are tightened to a snug fit and strap 52 is tightened sufficiently until upper portions 46, 51 of medial and lateral condylar pads 34, 36 press into medial supracondylar hollow 48 and lateral supracondylar depression 50.

Figure 5:
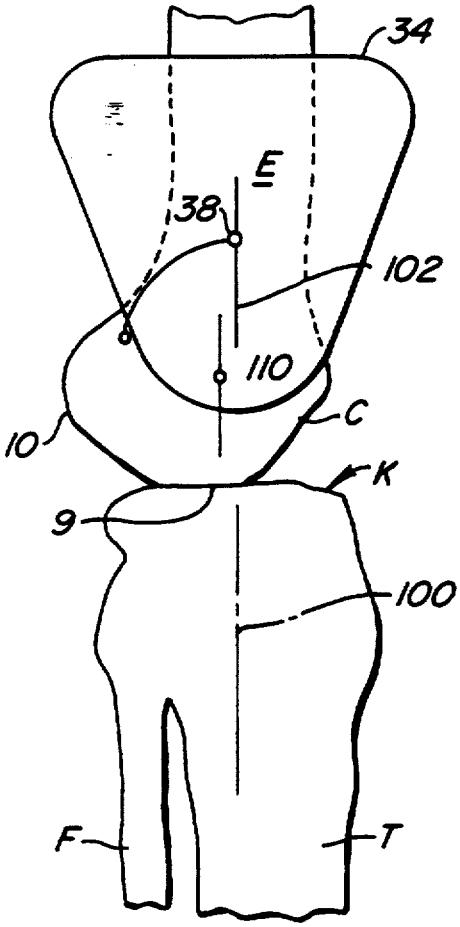
FIG. 5 is a view of a knee with the skeletal femur, tibia and fibula emphasized illustrating the extended position of the knee.
Figure 6:
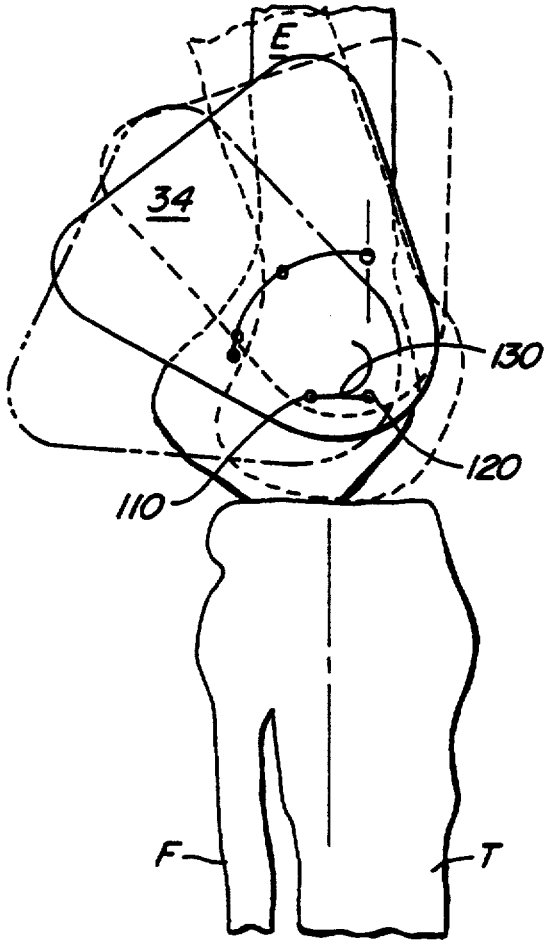
FIG. 6 is a skeletal diagram of the knee intermediately bent between full extension and full flexion.
Figure 7:
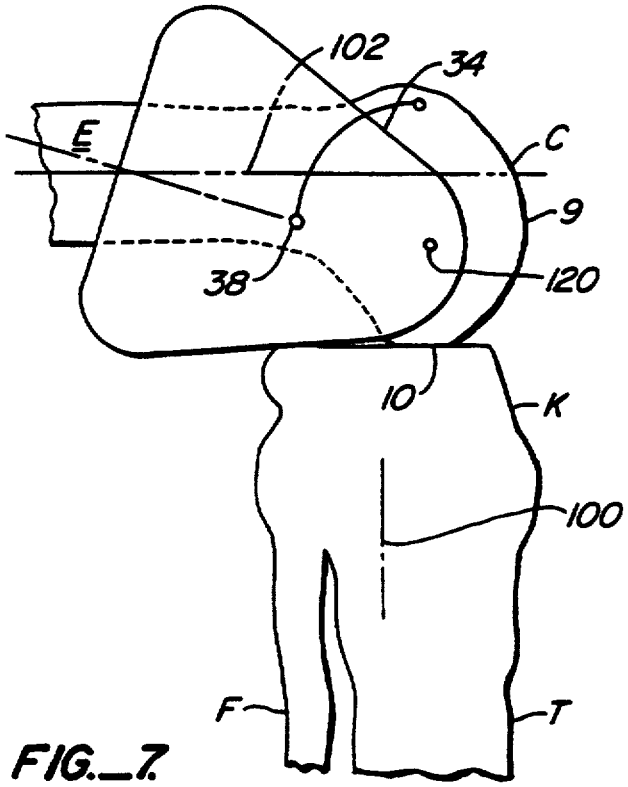
FIG. 7 is a skeletal diagram of the knee at or near full flexion.

Referring to FIGS. 5, 6 and 7, one of the supracondylar pads 34 is shown in all three views. Supracondylar pad is shown in positions of rotation as if it has rotated with respect to the flesh of the leg as the knee moved from the extended position (FIG. 5) to a position flexion (FIG. 7). During such movement, and with the disclosed 1⅛" offset between the hinge axis 42 and the axis of pivot 38, relative rotation of the pad occurs with respect to the femur E.

During this movement with the geometry herein set forth, the hinge axis 42 of the brace will be approximately coincident with the centers of pivot of the knee in all positions. Accordingly, the hinge axis will overlie center 110 of FIG. 5 when the knee is in the extended position. Likewise, it will overlie center of pivot 120 when the knee is near flexion. The track of movement of the hinge axis will approximate the movement of the center of pivot along track 130 as shown in FIG. 6.

Other modification and variation can be made to the disclosed embodiment without department from the subject of the invention as defined in the following claims. For example, medial and lateral condylar pads 34,36 are mounted to pivot about a generally horizontal axis 40 generally parallel to knee axis 44; they could be mounted to move in other manners and to pivot about other axis as well. Also the pivot axes for pads 34, 36 are colinear; they could be offset as well.

What is claimed is:

1. An improved knee brace comprising:

a thigh brace portion mountable to the user's upper leg, said thigh brace portion including medial and lateral struts, said struts extending rigidly from said thigh brace portion downwardly to and through a hinge axis;

a lower leg portion, said lower leg portion including medial and lateral struts extending upwardly from said lower leg portion to and towards a hinge axis on either side of said leg;

a simple hinge mounted between said upper and lower struts on both sides of said knee brace, said simple hinge enabling pivot of said thigh brace portion relative to said lower leg portion along a first substantially horizontal hinge axis between positions of extension and flexion when mounted to the knee of a wearer;

medial and lateral condylar pads pivotally secured to the thigh brace portion of pivotal movement generally along a second substantially horizontal medial and lateral pivot pad axis, parallel to but offset from said first substantially horizontal hinge axis of said simple hinge, said second substantially horizontal medial and lateral pivotal pad axis spaced apart from the above the first substantially horizontal axis of said hinge of said brace by a distance enabling articulation of said simple hinge axis from said thigh brace portion to follow the changing center of pivot of said knee during extension and flexion of said knee.

2. The invention of claim 1 and wherein said offset between said first substantially horizontal hinge axis and said second substantially horizontal medial and lateral pivot pad axis is in the range of ⅞ of an inch to 1⅜ inches.

3. In a knee brace having, a thigh brace portion mountable to the user's upper leg, said thigh brace portion including medial and lateral struts, said struts extending rigidly from said thigh brace portion downwardly to and through a hinge axis;

a lower leg portion, said lower leg portion including medial and lateral struts extending upwardly from said lower leg portion to and towards a hinge axis on either side of said leg;

a simple hinge mounted between said upper and lower struts on both side of said knee brace, said simple hinge enabling pivot of said thigh brace portion relative to said lower leg portion along a first substantially horizontal hinge axis between position of extension and flexion when mounted to the knee of said wearer; the improvement to said knee brace including;

medial and lateral condylar pads pivotally secured to the thigh brace portion of pivotal movement generally along a second substantially horizontal medial and lateral pivot pad axis, parallel to but offset from said hinge axis of said simple hinge, said second substantially horizontal medial and lateral pivot pad axis spaced apart from and above the first substantially horizontal axis of said hinge of said brace by a distance enabling articulation of said simple hinge axis from said thigh brace portion to follow the changing center of pivot of said knee during extension and flexion of said knee.

4. The invention of claim 1 and wherein said offset between said first substantially horizontal hinge axis and said second substantially horizontal medial and lateral pivot pad axis is in the range of $\frac{7}{8}''$ to $1\frac{3}{8}''$.

*5. An improved knee brace comprising:*

*a thigh brace portion mountable to the user's upper leg, said thigh brace portion including medial and lateral struts, said struts extending rigidly from said thigh brace portion downwardly to and through a hinge axis;*

*a lower leg portion, said lower leg portion including medial and lateral struts extending upwardly from said lower leg portion to and towards a hinge axis on either side of said leg;*

*a hinge mounted between said upper and lower struts on both sides of said knee brace, said hinge enabling pivot of said thigh brace portion relative to said lower leg portion along a first substantially horizontal hinge axis between positions of extension and flexion when mounted to the knee of a wearer;*

*medial and lateral condylar pads pivotally secured to the thigh brace portion for pivotal movement generally along an substantially horizontal medial and lateral pivot pad axis, said pads configured to conform to the user's medial and lateral supracondylar hollows;*

*said medial and lateral condylar pads inwardly deflected toward the femur above the femur condyle for capture to the respective medial supracondylar hollow and lateral supracondylar depression to restrain brace downward movement above the knee joint at a point superior to the center of pivot of condyle of the femur over the plateau of the tibia;*

*strap means passed around said medial and lateral condylar pads to exert when tightened on said medial and lateral condylar pads to produce a snug fit with said medial and lateral supracondylar hollow to restrain pistoning movement of said thigh brace portion towards the joint of the user's knee.*

* * * * *